United States Patent [19]

Ebel et al.

[11] Patent Number: 4,886,882
[45] Date of Patent: Dec. 12, 1989

[54] HYDROXYOXAALKYLMELAMINES

[75] Inventors: Klaus Ebel, Ludwigshafen; Wolfgang Reuther, Heidelberg, both of Fed. Rep. of Germany

[73] Assignee: BASF Aktiengesellschaft, Ludwigshafen, Fed. Rep. of Germany

[21] Appl. No.: 897,261

[22] Filed: Aug. 18, 1986

[30] Foreign Application Priority Data

Sep. 7, 1985 [DE] Fed. Rep. of Germany ....... 3531912

[51] Int. Cl.⁴ ........................................... C07D 251/70
[52] U.S. Cl. ..................................................... 544/196
[58] Field of Search ......................... 544/196, 205, 194

[56] References Cited

U.S. PATENT DOCUMENTS

| | | | |
|---|---|---|---|
| 2,328,961 | 9/1943 | D'Alelio et al. | 544/196 |
| 3,256,281 | 6/1966 | Kaiser et al. | 544/196 |
| 3,265,668 | 8/1966 | Dowbenko et al. | 544/196 |
| 3,278,253 | 10/1966 | Weckler et al. | 544/196 |
| 3,573,301 | 3/1971 | Winter | 544/196 |
| 4,356,304 | 10/1982 | Szita et al. | 544/205 |
| 4,668,785 | 5/1987 | Ebel et al. | 544/196 |
| 4,711,679 | 12/1987 | Gilbert | 544/196 |

FOREIGN PATENT DOCUMENTS 49-39272 10/1974 Japan .................................. 544/196

Primary Examiner—John M. Ford
Attorney, Agent, or Firm—Keil & Weinkauf

[57] ABSTRACT

Hydroxyoxaalkylmelamines of the general formula I

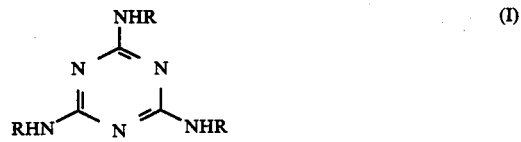

where the radicals R may be identical or different and are each hydrogen or a radical of the general formula II

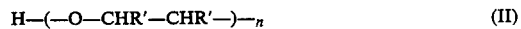

where the radicals R' may be indentical or different and are each hydrogen or $C_1$-$C_4$-alkyl and n is 2 or 3, and mixtures of these, are useful intermediates for the preparation of urethanes and for modifying aminoplast resins.

2 Claims, No Drawings

HYDROXYOXAALKYLMELAMINES

The present invention relates to novel hydroxyoxaalkylmelamines, in particular N-mono, N,N'-bis- and N,N',N''-tris-(5-hydroxy-3-oxapentyl)-melamine, processes for the preparation of the pure compounds and of mixtures of these compounds, and their use.

US-A-4 312 988 discloses the reaction of melamine with ethanolamine or with isopropanolamine. It was found that, instead of N,N',N''-tris-(2-hydroxyethyl)-melamine being obtained in the reaction of melamine with ethanolamine, principally isomelamines are formed in a competing reaction with elimination of water, these isomelamines being responsible for the low yield of N,N',N''-tris-(2-hydroxyethyl)-melamine. For example, in the reaction of ethanolamine with melamine in a molar ratio of 3.2:1, 20% of isomelamines were obtained at a conversion of 82%, as much as 50% of isomelamines at a conversion of 95%, and finally 100% of isomelamines at a conversion of 99%.

The use of isopropanolamine instead of ethanolamine has therefore been proposed. According to US-A-4 312 988, it should be possible drastically to reduce the formation of isomelamine if the straight-chain compound ethanolamine is replaced with a branched isoalkanolamine.

However, in the example described there, in which isopropanolamine and melamine are reacted, it is evident that the end product obtained still contains 40% of the undesirable isomelamines.

The present invention relates to hydroxyoxaalkylmelamines of the general formula I

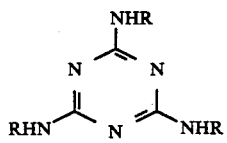
(I)

where the radicals R may be identical or different and are each hydrogen or a radical of the general formula II

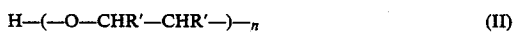
(II)

where the radicals R' may be identical or different and are each hydrogen or $C_1$-$C_4$-alkyl and n is 2 or 3, and mixtures of these. $C_1$-$C_4$-alkyl radicals R' may be methyl, ethyl, n-propyl, isopropyl or butyl.

Preferred hydroxyoxaalkylmelamines are those in which R in the general formula I is hydrogen or 5-hydroxy-3-oxapentyl of the formula III

(III).

N-Mono-(5-hydroxy-3-oxapentyl)-melamine, N,N'-bis-(5-hydroxy-3-oxapentyl)-melamine and N,N',N''-tris-(5-hydroxy-3-oxapentyl)-melamine and mixtures of these are particularly preferred.

The compounds of the general formula IV are preferably obtained in the course of aminating ethylene oxide or propylene oxide. Hence, R' in the radical of the general formula II is hydrogen or methyl, and in particular the combination R'/R' is H/H or H/CH$_3$.

The present invention furthermore relates to a process for the preparation of the compounds of the general formula I, wherein melamine is reacted with a compound of the general formula IV

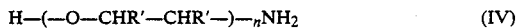
(IV)

where R' and n have the above meanings, at from 120° to 250° C. in the presence of an acidic catalyst.

Surprisingly, it has been found that the isomelamines formed in the known process can be completely excluded if the amine is replaced by, for example, 2,2'-aminoethoxyethanol. N,N',N''-Tris-(5-hydroxy-2-oxapentyl)-melamine is obtained in quantitative yield and more than 95% purity. By terminating the reaction, it is also possible to prepare defined mixtures of the tris and bis compounds or of the tris, bis and mono compounds in a reproducible manner.

Compared with the reaction with the lower boiling alkanolamines ethanolamine (bp.=170° C.) and isopropanolamine (bp.=160° C.) by the prior art, the higher boiling 2,2'-aminoethoxyethanol has the additional advantage of shorter reaction times (bp.=218° C.).

The process is advantageously carried out by initially taking a mixture of melamine, 2,2'-aminoethoxyethanol (formula: H$_2$N—CH$_2$—CH$_2$—O—CH$_2$—CH$_2$—OH), the acidic catalyst and, if required, a solvent, and heating the stirred mixture at from 120° to 250° C., in particular from 150° to 230° C.

The process is carried out in general under atmospheric pressure, but in order to reach the upper temperature range (from 230° to 250° C.), a pressure of from 1 to 15 bar must be maintained.

It is also advisable to carry out the reaction in the presence of a protective gas, the latter generally being passed over the surface of the reaction mixture. Examples of suitable protective gases are noble gases and in particular nitrogen.

Suitable acidic catalysts are all strong and moderately strong acids, eg. hydrofluoric acid, hydrochloric acid, hydrobromic acid, sulfuric acid, nitric acid, phosphoric acid, amidosulfonic acid, thiocyanic acid, p-toluenesulfonic acid and methanesulfonic acid.

The acids can be added either in free form or as melamine or amine salts. They may also be added in the form of a salt of a base which is weaker than 2,2'-aminoethoxyethanol, for example as the ammonium salt.

Instead of the stated protic acid, the reaction can also be catalyzed by Lewis acids, such as boron trifluoride, aluminum chloride, tin(IV) chloride, antimony(V) fluoride or iron(III) bromide.

From 0.05 to 3 moles, preferably from 0.1 to 1 mole, of catalyst are advantageously employed per mole of melamine. The reaction rate is found to increase as the amount of catalyst increases.

The novel process is preferably carried out in the absence of a solvent, although an organic solvent may be employed. Polyols, eg. ethylene glycol, 1,2-propylene glycol, diethylene glycol or triethylene glycol, are suitable for this purpose.

The 2,2'-aminoethoxyethanol can be used in any amount. However, an excess of amine is preferably employed, usually from 3 to 10 moles of amine per mole of melamine.

The course of the reaction can be monitored by analytical methods, for example by high pressure liquid chromatography (HPLC). The reaction may be terminated at any conversion, mixtures of N,N',N''-tris-(5-hydroxy-3-oxapentyl)-melamine, N,N'-bis-(5-hydroxy- 3-oxapentyl)-melamine and, if appropriate, N-mono-(5-hydroxy-3-oxapentyl)-melamine being obtained; these mixtures have a defined, reproducible composition.

On complete conversion, pure N,N',N''-tris-(5-hydroxy-3-oxapentyl)-melamine is obtained.

To isolate the desired products, the particular catalyst is advantageously neutralized by adding a base, eg. sodium hydroxide, potassium hydroxide, sodium carbonate, potassium carbonate, calcium carbonate or barium carbonate, to the reaction mixture and isolating the precipitated salts.

Thereafter, excess free 2,2'-aminoethoxyethanol is distilled off under reduced pressure (about 15 mbar) at about 180° C., the virtually colorless residue solidifying to a resin.

In another embodiment, the present invention relates to an alternative process for the preparation of compounds of the general formula I. In the process, a chlorotriazine of the general formula V

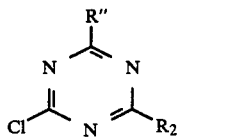

(V)

where the radicals R'' may be identical or different and are each Cl or NH$_2$, is reacted with a compound of the general formula IV

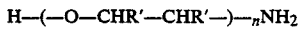

(IV)

where R' and n have the meanings stated in claim 1, in the presence of a base.

The chlorotriazine used as the starting compound is diaminochlorotriazine, dichloroaminotriazine or cyanuric chloride. Pure compounds are obtained in each case.

The base employed may be any base, but the process is advantageously carried out in water with the addition of sodium hydroxide solution (cf. J. Am. Chem. Soc. 73, (1951), 2984–2986) or in dioxane with the addition of potassium carbonate (cf. US-A-3 537 301).

The desired products are then isolated in a conventional manner.

The oxaalkanolamines of the general formula II which are used as starting compounds are either known or can be prepared by known methods (cf. M. S. Malinskii, A. N. Korchagina, A. G. Yudasina and D. G. Yurko, Vorpr. Khim. Khim. Teknol., 34 (1974), 6–11 (Russian) and Jpn. Kokai JP-A-79 03 005, Application No. 77/67,803).

The chlorotriazines of the general formula V are known compounds.

The novel compounds according to the invention are useful intermediates for the preparation of urethanes and are also very suitable for modifying aminoplast resins.

The Examples which follow illustrate the invention.

EXAMPLE 1

N,N',N''-Tris-(5-hydroxy-3-oxapentyl)-melamine 111.0 g (0.6 mole) of cyanuric chloride, 160 g of anhydrous potassium carbonate and 210.0 g (2.0 moles) of 2,2'-aminoethoxyethanol in 1.2 l of dioxane were refluxed for 5 hours and then filtered under suction while hot, and the filtrate was evaporated to dryness. 229 g (98%) of a pale yellow resin were obtained. Before being analyzed, the product was crystallized from water, colorless crystals of melting point 68° C. being obtained.

1H-NMR. δ(ppm)=3.4 ppm (s, 24H); 4.4 (s, broad, 3H) 6.4 ppm (s, broad, 3H).

Analysis

|  | C | H | N | O |
|---|---|---|---|---|
| calculated: | 46.1 | 7.7 | 21.5 | 24.6 |
| found: | 45.8 | 7.6 | 21.2 | 24.9. |

EXAMPLE 2

N,N'-Bis-(5-hydroxy-3-oxapentyl)-melamine 47.3 g (0.45 mole) of 2,2'-aminoethoxyethanol were added dropwise to a suspension of 33.0 g (0.2 mole) of dichloroaminotriazine in 200 ml of water. The mixture was then heated to 100° C., and the pH was kept at 8–9 by adding 25% strength sodium hydroxide solution. When the alkali was no longer consumed, the mixture was left to cool and evaporated to dryness under reduced pressure. The residue was boiled with 250 ml of isopropanol, and the insoluble sodium chloride was filtered off. The filtrate was freed from the solvent under reduced pressure, and 59 g (98%) of a colorless resin were obtained. Before being analyzed, the product was subjected to distillation in a bulb tube apparatus (200° C./0.1 mbar).

1H-NMR. δ(ppm)=3.4 ppm (s, 16H); 4.5 (s, broad, 3H); 6.0 (s, broad, 2H) 6.4 ppm (s, broad, 2H).

Analysis

|  | C | H | N | O |
|---|---|---|---|---|
| calculated: | 43.7 | 7.3 | 27.8 | 21.2 |
| found: | 43.7 | 7.3 | 27.4 | 21.5. |

EXAMPLE 3

N-Mono-(5-hydroxy-3-oxapentyl)-melamine 58.2 g (0.40 mole) of diaminochlorotriazine and 47.3 g (0.45 mole) of 2,2'-aminoethoxyethanol in 300 ml of water were refluxed, and the pH was kept at 8–9 by metering in 25% strength sodium hydroxide solution. When the reaction was complete, the clear solution was left to cool, the product crystallizing out. It was filtered off under suction and dried, and 74.3 g (87%) of colorless crystals of melting point 108° C. were obtained. Before being analyzed, the product was recrystallized from water.

1H-NMR. δ(ppm)=3.4 ppm (s, 8H); 4.5 (s, broad, 1H); 6.0 (s, broad, 4H) 6.4 ppm (s, broad, 1H).

Analysis

|  | C | H | N | O |
|---|---|---|---|---|
| calculated: | 39.2 | 6.6 | 39.2 | 14.9 |
| found: | 39.1 | 6.5 | 38.7 | 16.0. |

EXAMPLE 4

Preparation of N,N',N''-tris-(5-hydroxy-3-oxapentyl)-melamine from melamine 37.5 g (0.4 mole) of concentrated sulfuric acid were added dropwise to a stirred mixture of 229 g (1.8 moles)

of melamine and 1530 g (15.6 moles) of 2,2'-aminoethoxyethanol. The mixture was then refluxed for about 10–12 hours at from 210°–220° C. until conversion was complete, while stirring and passing over a gentle stream of nitrogen. Finally, the bisulfate was decomposed by adding 58.3 g of 50% strength sodium hydroxide solution and the precipitated sodium sulfate was filtered off hot. Distilling off the excess aminoethoxyethanol under reduced pressure gave 702 g (100%) of a pale yellow resin which was shown by quantitative HPLC analysis to consist of 96–98% of pure N,N',N''-tris-(5-hydroxy-3-oxapentyl)-melamine (comparative substance, see Example 1). The $^1$H—NMR spectrum too was in agreement with the spectrum of the substance from Example 1.

EXAMPLE 5

Mixture of mono-, N,N'-bis- and N,N',N''-tris-(5-hydroxy-3-oxapentyl)-melamine 78.4 g (0.8 mole) of concentrated sulfuric acid were added dropwise to a stirred mixture of 504 g (4.0 moles) of melamine and 1682 g (16.0 moles) of 2,2'-aminoethoxyethanol and 993 g (16.0 moles) of ethylene glycol. The mixture was then refluxed for about 3 hours at from 200° to 210° C. while stirring and passing over a gentle stream of nitrogen. To work up the mixture, 128 g (0.8 mole) of 50% strength sodium hydroxide solution were added and the precipitated sodium sulfate was filtered off. Finally, the excess amine and the glycol were distilled off under reduced pressure to give 1150 g (100%) of a pale yellow resin whose composition, determined by HPLC, is as follows:

about 4 mol% of melamine, 26 mol% of mono-(5-hydroxy-3-oxapentyl)-melamine, 52 mol% of N,N'-bis-(5-hydroxy-3-oxapentyl)-melamine and 18 mol% of N,N',N''-tris-(5-hydroxy-3-oxapentyl)-melamine.

EXAMPLE 6

Mixture of N,N'-bis- and N,N',N''-tris-(5-hydroxy-3-oxapentyl)-melamine 39.2 g (0.4 mole) of concentrated sulfuric acid were added dropwise to a stirred mixture of 252 g (2.0 moles) of melamine, 1050 g (10.0 moles) of 2,2'-aminoethoxyethanol and 372 g (6.0 moles) of ethylene glycol. The reaction was carried out similarly to Example 5, and the mixture was worked up as in Example 5 with 64 g (0.8 mole) of 50% strength sodium hydroxide solution, and 727 g (100%) of a mixture of 40% of N,N'-bis- and 60% of N,N',N''-tris-(5-hydroxy-3-oxapentyl)-melamine (HPLC) were obtained after a reaction time of about 6 hours.

We claim:

1. A hydroxyoxaalkylmelamine of the formula I

(I)

where the radicals R may be hydrogen or the 5-hydroxy-3-oxapentyl radical of the formula III

HO—CH$_2$—CH$_2$—O—CH$_2$—CH$_2$—    (III), with the proviso that at least one of the R radicals is a radical of the formula III.

2. A hydroxyoxaalkylamine of the formula I as described in claim 1, wherein R in each instance is 5-hydroxy-3-oxapentyl.

* * * * *